United States Patent
Yamamori

(10) Patent No.: US 7,001,939 B2
(45) Date of Patent: Feb. 21, 2006

(54) HIGH AMYLOSE WHEAT STARCH AND WHEAT CONTAINING THE SAME

(75) Inventor: Makoto Yamamori, Ibaraki (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 548 days.

(21) Appl. No.: 09/841,787

(22) Filed: Apr. 24, 2001

(65) Prior Publication Data

US 2003/0208806 A1 Nov. 6, 2003

Related U.S. Application Data

(62) Division of application No. 09/325,819, filed on Jun. 4, 1999.

(51) Int. Cl.
- C08L 89/00 (2006.01)
- C13F 3/00 (2006.01)
- C08B 30/00 (2006.01)
- C08B 35/00 (2006.01)
- A23B 4/03 (2006.01)

(52) U.S. Cl. ............... 524/47; 127/29; 127/32; 127/38; 127/65; 127/67; 127/71; 106/649; 106/652; 106/724; 106/730; 106/805; 426/463; 426/484; 426/622; 536/102; 536/56

(58) Field of Classification Search ............ 524/47; 127/29–71; 106/649–805; 426/463–622, 426/74, 94; 536/102, 56; 800/320.3
See application file for complete search history.

(56) References Cited

PUBLICATIONS

Technology of Cereals (4th edition) by Kent, N.L.; Evers, A.D.; 1994; Pergamon, pp 53–77.*
M. Takaoka, et al., *J. Agric. Food Chemistry*, vol. 45, No. 8, pp. 2929–2934 (1997).
M. Yamamori, et al., *Theor. Appl. Genet.*, 93, pp. 275–281 (1996).
O. Nelson, et al., *Annu. Rev. Plant Physiol. Plant Mol. Biol.*, 46, pp. 475–488 (1995).
H. Satoh, *Nippon Nogeikagaku Kaishi*, vol. 68, No. 11, pp. 1577–1580 (1994).
L. Curtis Hannah, et al., *Scientia Horticulturae*, 55, pp. 177–184 (1993).
M. Gao, et al., *The Plant Cell*, vol. 10, pp. 399–412 (Mar. 1998).
J.C. Shannon et al., *Genetics and Physiology of Starch Development*, Chapter III, pp. 56–59 (1984).

* cited by examiner

*Primary Examiner*—Anne Marie Grunberg
(74) *Attorney, Agent, or Firm*—Townsend and Townsend and Crew LLP

(57) ABSTRACT

Wheat starch of the present invention is obtained from endosperm of a seed of wheat which is modified to lack starch granule protein-1 (SGP-1). The wheat starch has an apparent amylose content of about 35% or more. Wheat flour of the present invention is obtained from endosperm of a seed of wheat which is modified to lack SGP-1. Wheat of the present invention is modified to lack SGP-1. The wheat flour and the wheat comprise wheat starch which has an apparent amylose content of about 35% or more.

5 Claims, 1 Drawing Sheet

HIGH AMYLOSE WHEAT STARCH AND WHEAT CONTAINING THE SAME

This application is a divisional of U.S. application Ser. No. 09/325,819 filed Jun. 4, 1999, the disclosure of which is being incorporated by reference for all purposes.

BACKGROUND OF THE INVENTION

1. Field of the Invention

The present invention relates to wheat starch having novel properties and, more particularly, to wheat starch having a high apparent amylose content.

2. Description of the Related Art

Starch is the major component of the endosperm of a cereal seed such as wheat. Wheat starch components can be either amylose or amylopectin. The amylose content of wheat starch is 0% for waxy wheat cultivars and about 22–30% (about 29% on average) for normal (non-waxy) wheat cultivars.

Some maize cultivars yield corn starch in which the amylose content is as high as about 60–70%. Corn starch with high amylose content provides various industrial applications, such as an adhesive for cardboard, a converging agent for glass fiber and an edible film, as well as food applications such as ricemeal which is used when making rice cake.

Among various rice varieties, Indica rice grain has a higher amylose content than Japonica rice grain. Rice grains having a high amylose content can be suitably used for pilaf and rice vermicelli.

Wheat starch with a high amylose content and wheat flour containing such wheat starch are expected to provide new industrial and food applications. Therefore, attempts have been made to produce wheat starch with increased amylose content using crossbreeding and genetic engineering approaches. However, to the extent the present inventor is aware of, no satisfactory results have been obtained.

Amylose is an α(1,4)-linked glucose polymer which is essentially a linear chain without branching. Amylopectin is a branched glucose polymer in which branch chains are linked to the main chain of α(1,4)-linked polymer by α(1,6)-linkages. The linear glucose polymers are synthesized by the action of starch synthases which produces (1,4)-linkages. The (1,6)-linkages of amylopectin are produced by the action of branching enzymes.

Studies in pea, maize, and wheat (Denyer et al., Plant J. 4:191–198, 1993; Echt and Schwartz, Genetics 99:275–284, 1981; Mu et al., Plant J. 6:151–159, 1994; and Denyer et al., Planta 196:256–265, 1995) have shown that some enzymes for starch synthesis are tightly bound to starch granules from seed endosperms of maize and wheat and pea embryo.

The detailed mechanism for the binding of these enzymes to starch granules has been unknown. However, it is believed that in wheat, at least four kinds of proteins, i.e., waxy protein and three starch granule proteins (SGP-1, SGP-2, SGP-3), are tightly bound to starch granules and are responsible for starch synthesis. Waxy protein, i.e., granule-bound starch synthase I (GBSS I) responsible for amylose synthesis, is the product of the waxy gene (Ainsworth et al., Plant Mol Biol. 22:67–82, 1993). SGP-1, -2 and -3 (Yamamori and Endo, Theor Appl. Genet. 93:275–281, 1996) correspond to starch granule-bound isozymes of about 100–105 kDa, about 90 kDa and about 77 kDa, respectively, reported by Denyer et al. (Planta, supra). Immunoblotting, amino acid sequencing and detection of starch synthase or branching activities (Denyer et al., Planta, supra; Rahman et al., Aust. J. Plant Physiol. 22:793–803, 1995; Takaoka et al., J. Agric. Food Chem. 45:2929–2934, 1997) suggest that SGP-2 is a homolog of maize branching enzyme IIb (Fisher et al., Plant Physiol. 102:1045–1046, 1993) and that SGP-3 is a homolog of maize starch synthase I (Knight et al., Plant J. 14:613–622, 1998).

Immunoblotting studies on about 100–105 kDa protein (SGP-1) did not detect the protein in the soluble fraction. Thus, SGP-1 is exclusively bound to starch granules (Denyer et al., Planta, supra; Rahman et al., supra). This protein is presumed to be a starch synthase from the studies of antiserum recognition, enzymatic activity detected and homology in amino acid sequences (Denyer et al., Planta, supra; Takaoka et al., supra). However, information regarding the physiological function of SGP-1 in vivo has been limited. For maize, it has been reported that an apparent amylose content is increased in a mutant of dull 1 gene which is presumed to code for starch synthase II (Gao et al., The Plant Cell 10:399–412, 1998). However, there is no substantial amino acid sequence homology between the protein coded by dull 1 (Gao et al., supra) and the protein SGP-1 of wheat (Takaoka et al., supra). Further, the protein coded by dull 1 is present in the soluble fraction. Thus, the starch synthase encoded by dull 1 is significantly different from SGP-1.

A hexaploid wheat has three isozymes of SGP-1, i.e., SGP-A1, SGP-B1 and SGP-D1. The gene coding for SGP-A1, Sgp-A1, is located on chromosome arm 7A, Sgp-B1 on 7B, and Sgp-D1 on 7D (Denyer et al., Planta, supra). Using SDS-polyacrylamide gel electrophoresis (SDS-PAGE), it has been found that a few wheat cultivars lacked either SGP-A1, -B1 or -D1, but no wheat cultivars lacked two or more SGP-1s (Yamamori and Endo, supra).

SUMMARY OF THE INVENTION

According to one aspect of this invention, there is provided wheat starch obtained from endosperm of a seed of wheat which is modified to lack starch granule protein-1 (SGP-1). The wheat starch has an apparent amylose content of about 35% or more.

According to another aspect of this invention, there is provided wheat flour obtained from endosperm of a seed of wheat which is modified to lack SGP-1. The wheat flour includes wheat starch which has an apparent amylose content of about 35% or more.

According to still another aspect of this invention, there is provided wheat which is modified to lack SGP-1. The wheat includes wheat starch which has an apparent amylose content of about 35% or more.

In one embodiment, the apparent amylose content may be from about 30% to about 45%, preferably from about 37% to about 40%.

In one embodiment, the wheat may be a hexaploid wheat which lacks SGP-A1, SGP-B1 and SGP-D1. The hexaploid wheat may be obtained by crossing a first wheat lacking a first protein selected from the group consisting of SGP-A1, SGP-B1 and SGP-D1, with a second wheat lacking a second protein which differs from the first protein and is selected from the group consisting of SGP-A1, SGP-B1 and SGP-D1, followed by further crossing the cross of the first wheat and the second wheat with a third wheat lacking a third protein which differs from the first and second proteins and is selected from the group consisting of SGP-A1, SGP-B1 and SGP-D1. The hexaploid wheat may be obtained by crossing (i) Chousen 30 or Chousen 57, (ii) Turkey 116, and (iii) Kanto 79 in an arbitrary order.

Thus, the invention described herein makes possible the advantage of providing wheat starch having a high apparent amylose content.

This and other advantages of the present invention will become apparent to those skilled in the art upon reading and understanding the following detailed description with reference to the accompanying figures.

DESCRIPTION OF THE PREFERRED EMBODIMENTS

Figure 1:
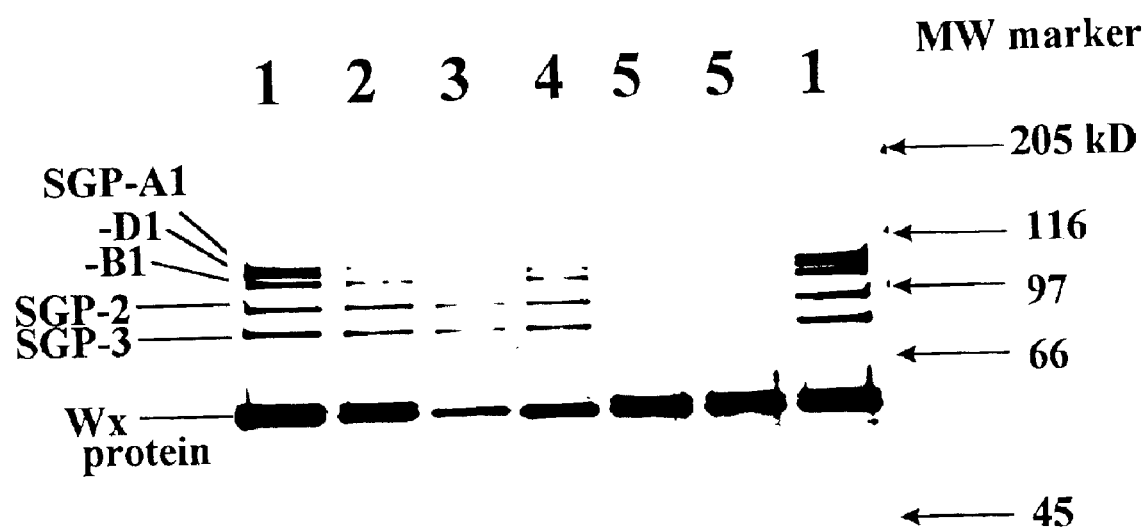
FIG. 1 is a photograph of a gel developing an electrophoresis pattern of wheat lacking one or more SGP-1s. Lane 1 shows Chinese Spring as a control; lane 2 shows Turkey 116 (Parent); lane 3 shows Kanto 79 (Parent); lane 4 shows Chousen 57 (Parent); and lane 5 shows SGP-1 null wheat.

Hereinafter, the present invention will be described in greater detail.

1. Definitions

"SGP-1" is one of several kinds of proteins referred to as starch granule proteins, or "SGPs", which are not washed off, but remain bound to, starch granules of wheat seed endosperms during a process for washing the starch granules with a buffer containing a surfactant, sodium dodecyl sulfate (SDS). Recent reports have shown that SGP-1 is a starch synthase. Hexaploid wheat having genome organization of AABBDD has three isozymes of SGP-1, i.e., SGP-A1, -B1 and -D1. Tetraploid wheat having genome organization of AABB has two isozymes of SGP-1, i.e., SGP-A1 and -B1. These isozymes of SGP-1 can be detected and identified by SDS-gel electrophoresis as three distinguished protein bands. Specifically, SGP-A1, -B1 and -D1 are detected by SDS-gel electrophoresis as bands of about 115 kDa, about 100 kDa and about 108 kDa, respectively (Yamamori and Endo, supra).

Herein, the terms "SGP-1", "SGP-A1", "SGP-B1"and "SGP-D1" are used to denote proteins, while "Sgp-1", "Sgp-A1", "Sgp-B1" and "Sgp-D1" are used to denote genes coding for the proteins, SGP-1, SGP-A1, SGP-B1 and SGP-D1, respectively.

The phrase "lacking" SGP-1 as used herein means that any SGP-1 protein is not expressed at a level detectable in SDS-gel electrophoresis. More specifically, it means that the band of the protein of interest is substantially undetectable by silver staining which is a sensitive method for protein detection.

The term "apparent amylose content" as used herein refers to an amylose content as measured by colorimetric measurement based on iodine coloration using an autoanalyzer or by amperometric titration based on iodine affinity. In the context of the present invention, when it is stated that wheat has an apparent amylose content of "about 35% or more", for example, means that the wheat has an amylose content of about 35% or more as measured under conditions that are substantially the same as those used in either the calorimetric measurement as described in section (1) of Example 4 below or the amperometric titration as described in section (2) of Example 4 below, or both.

The wheat starch herein disclosed can also be characterized by maximum absorbance ($\lambda_{max}$) and absorbance at 680 nm (blue value). As measured under substantially the same conditions as those of Example 3 below, the wheat starch may have $\lambda_{max}$ of from about 600 nm to about 620 nm, and blue value of from about 0.45 to about 0.55.

"Wheat" refers to a plant belonging to the genus Triticum. Wheat includes "hexaploid wheat" which has genome organization of AABBDD, comprised of 42 chromosomes, and "tetraploid wheat" which has genome organization of AABB, comprised of 28 chromosomes. Hexaploid wheat includes *T. aestivum, T. spelta, T. macha, T. compactum, T. sphaerococcum, T. vavilovii*, and interspecies cross thereof. Tetraploid wheat includes *T. durum, T. dicoccoides, T. dicoccum, T. polonicum*, and interspecies cross thereof. A wheat cultivar for use in the present invention may belong to any of the above-listed species, and preferably a hexaploid wheat, and more preferably *T. aestivum*.

"Modified" wheat as used herein refers to wheat which has been artificially manipulated to lack SGP-1, and it is intended to exclude naturally-occurring wheat. The artificial manipulation of wheat is typically, but not limited to, cross breeding. It may be any other appropriate manipulation, including mutagenesis and genetic recombination.

"Kanto 79/Turkey 116" as used herein refers to a cross obtained by pollinating Kanto 79 with pollen of Turkey 116. "(Kanto 79/Turkey 116)$F_2$//Chousen 57" as used herein refers to a cross obtained by first pollinating Kanto 79 with pollen of Turkey 116 to obtain a plant ($F_1$), self-pollinating the plant ($F_1$) to obtain a new progeny plant ($F_2$), and then pollinating the progeny plant ($F_2$) with pollen of Chousen 57.

2. Production of Wheat Lacking SGP-1 (SGP-1 Null Wheat)

As a method for completely eliminating all SGP-1 proteins from hexaploid wheat, the present inventors have developed a novel method as will be described below. It is noted that as a pollen parent for the crossing process which will be described below, either of the parent wheat cultivars can be used because SGP-1 is coded by a chromosomal gene.

First, a wheat cultivar lacking only SGP-D1 (Sgp-D1 null), for example, is crossed with another wheat cultivar lacking only SGP-B1 (Sgp-B1 null) so as to obtain $F_1$ seeds. Since a wheat cultivar is generally a homozygote, the obtained $F_1$ seeds will be heterozygous for both Sgp-D1 and Sgp-B1, whereby both SGP-D1 and SGP-B1 will be detected in the $F_1$ seed endosperms. When $F_1$ plants which have grown from the $F_1$, seeds are self-pollinated, $F_2$ seeds will segregate with regard to each of Sgp-D1 and Sgp-B1 alleles at the probability of one out of four (¼). That is, one out of four $F_2$ seeds will be null as to the Sgp-B1 gene, and independently, one out of four $F_2$ seeds will be null as to the Sgp-D1 gene. Thus, from the entire $F_2$ seed population, an $F_2$ seed being null as to both Sgp-D1 and Sgp-B1 is obtained by the probability of one out of sixteen (¹⁄₁₆; i.e., ¼ multiplied by ¼), theoretically.

Starches are purified from distal halves of the obtained $F_2$ grains, and examined for the presence or absence of SGP-D1 and SGP-B1 by subjecting to electrophoresis so as to select those lacking both SGP-D1 and SGP-B1. The proximal halves corresponding to the selected distal halves are seeded to obtain plants lacking both SGP-D1 and SGP-B1. The obtained plant is crossed with another wheat cultivar lacking only SGP-A1 (Sgp-A1 null) so as to obtain new $F_1$, seeds. The new $F_1$ seeds will be heterozygous for all of Sgp-A1, Sgp-B1 and Sgp-D1, and therefor all of SGP-A1, SGP-B1 and SGP-D1 will be detected in endosperms of the new $F_1$ seeds. When new $F_1$ plants which have grown from the new $F_1$ seeds are self-pollinated, new $F_2$ seeds will segregate with regard to each of Sgp-A1, Sgp-B1, and Sgp-D1 alleles at the probability of one out of four (¼). Thus, from the entire new $F_2$ seed population, a new $F_2$ seed being null as to all of Sgp-A1, Sgp-B1 and Sgp-D1 is obtained at the probability of one out of sixty-four (¹⁄₆₄; i.e., ¼ multiplied by ¼, further multiplied by ¼), theoretically.

Starches are purified from distal halves of the obtained new $F_2$ grains, and examined for the presence or absence of SGP-A1, -B1 and -D1 by subjecting the SGPs to electrophoresis so as to select those lacking all of SGP-A1, -B1 and -D1. The proximal halves corresponding to the selected distal halves are seeded to obtain plants lacking all of SGP-A1, -B1 and -D1.

While an exemplary crossing process has been described above, the order of crossing is not limited to the order described above. Wheat cultivars lacking only SGP-A1 (SOP-A1 null wheat) include Chousen 30, Chousen 57 and the like. Wheat cultivaus lacking only SOP-B1 (SGP.B1 null wheat) include Kanto 79, and the like. Wheat cultivars lacking only SGP-D1 (SGP-D1 null wheat) include Turkey 116, and the like. Seed for wheat lines Turkey 116 (Accession number FERM BP-08426), Kanto 79 (Accession number FERM BP-08423), Chousen 30 (Accession number FERM BP-08424) and Chousen 57 (Accession number FERM BP-08425) were deposited on Jul. 9, 2003 under the Budapest Treaty with the International Patent Organism Depositorj, National Institute of Advanced Industrial Science and Technology located at AIST Tsukubt Central 6, 1-1, Higashi 1-Chome Taukuba-shi, Ibaraki-ken 305–8566 Japan. Other such cultivars may be obtained by screening according to the method described in Yazuamori and Endo, supra.

Tetraploid wheat, e.g., durum wheat, which lacks SGP-1 can also be obtained in a manner similar to that for SGP-1 null hexaploid wheat. For example, SGP-1 null tetraploid wheat may be produced by first obtaining hexaploid wheat (2n=42) lacking both SGP-A1 and -B1, crossing the obtained hexaploid wheat with durum wheat, and then selecting progenies being tetraploid (2n=28) and lacking both SGP-A1 and -B1. Alternatively, SGP-1 null tetraploid wheat may be produced by first crossing two durum wheat cultivars which lack SGP-A1 and -B1, respectively, self-pollinating the obtained cross, and then selecting progenies which lack both SGP-A1 and -B1.

SGP-1 null hexaploid wheat may alternatively be produced by crossing tetraploid wheat lacking both SGP-A1 and -B1 with *Aegilops squarrosa* having genome organization of DD and lacking SGP-D1 so as to obtain triploid individuals, subjecting the obtained triploid individuals to a doubling of chromosomes such as a colchicine treatment so as to obtain hexaploid progeny, and then obtaining hexaploid progenies which lack all of SGP-A1, SGP-B1 and SGP-D1.

The present invention has been made based on a discovery that wheat lacking SGP-1 produces novel starch having a high level of apparent amylose content which, to the extent that the present inventor is aware of, has not been previously known in the art. Wheat starch and wheat flour of the present invention may be obtained by any method with which wheat lacking SGP-1 can be produced, and such method is not limited to the cross breeding as described above. For example, wheat lacking SGP-1 may alternatively be obtained by first treating wheat having SGP-1 with a mutagen, and then screening the treated wheat plant or progeny of the treated wheat plant obtained by self-pollinating the treated wheat plant, for the absence of all of SGP-A1, SGP-B1 and SGP-D1. Alternatively, when a wheat plant lacking one or two of SGP-A1, SGP-B1 and SGP-D1 is found in a wheat plant population obtained by a mutagenic treatment, crossing process(es) may further be performed using such wheat plant as a parental plant so as to obtain wheat plant lacking SGP-1.

The mutagen may be any appropriate mutagen including a physical mutagen such as ionizing radiation and a chemical mutagen. The physical mutagens include gamma ray, X ray, fast neutron, thermal neutron, beta ray, and the like. The chemical mutagens include ethyl methanesulfonate (EMS), N-methyl-N-nitrosourea (MNU), diethyl sulfate (dES), sodium azide ($NaN_3$), and the like. Appropriate methods for treating wheat plant with such mutagens, and appropriate conditions including what kind of wheat material is to be used with such a treatment are known to, and will be selected by, those skilled in the art.

Moreover, wheat lacking SGP-1 may alternatively be produced by any appropriate genetic engineering approach known in the art, including protoplast fusion, homologous recombination, antisense technique, and the like. Those skilled in the art can appropriately select one of these and other approaches, and combinations thereof.

3. Production of Wheat Starch and Wheat Flour with High Amylose Content

Wheat starch having the high amylose content of the present invention may be prepared by isolating starch from wheat seed lacking SGP-1 according to any appropriate method known in the art. Wheat flour having the high amylose content of the present invention may be prepared by milling the wheat seed lacking SGP-1 according to any appropriate method known in the art.

Wheat starch and wheat flour of the present invention are believed to be novel materials characterized by having a high level of apparent amylose content which has not been previously known in the art. Such wheat starch and wheat flour may be useful in various industrial and food applications. Moreover, wheat starch of the present invention may also be useful for the purpose of researching the correlation between the structure of glucose polymer and starch properties. Furthermore, modified wheat of the present invention may be useful as a breeding material for developing wheat which produces starch having an amylose content as high as that of maize (60%–70%).

EXAMPLES

Example 1

Production of Wheat Lacking SGP-1 (SGP-1 Null Wheat)

1. Plant Material

To produce a wheat which lacks SGP-1 (SGP-1 null wheat), the following four parental wheat (*Triticum aestivum* L.) cultivars were used: Chousen 30 (C 30) and 57 (C 57) lacking SGP-A1; Kanto 79 (K 79) lacking SGP-B1 and Turkey 116 (T 116) lacking SGP-D1 (see Table 1).

First, T 116 and K 79 were crossed to obtain $F_1$ seeds. $F_1$ plants which grew from the $F_1$ seeds were self-pollinated to obtain $F_2$ seeds. Starches were purified from the distal half of the $F_2$ seeds. SDS-polyacrylamide gel electrophoresis (SDS-PAGE) was performed using the purified starches so as to examine the presence or absence of SGP-D1 and -B1. As a result, $F_2$ seeds lacking both SGP-D1 and -B1 from cross K 79/T 116 were selected. Purification of the starches and SDS-PAGE will be described in greater detail below.

$F_2$ plants which grew from the selected $F_2$ seeds lacking both SGP-D1 and -B1 were pollinated by either of C 30 and C 57, both lacking SGP-A1, to obtain new $F_1$ seeds. New $F_1$ plants grown from the new $F_1$ seeds were self-pollinated to obtain new $F_2$ seeds. Starches were purified from the distal half of the new $F_2$ seeds. SDS-polyacrylamide gel electrophoresis (SDS-PAGE) was performed using the purified starches so as to examine the presence or absence of SGP-A1, -B1 and -D1. As a result, from the cross (K 79/T 116)$F_2$//C 30 or C 57, variant progeny (new $F_2$ plant) lacking SGP-1 was selected.

TABLE 1

Alleles for Sgp-1 in wheat materials used to produce wheat with no SGP-1 (SGP-1 null wheat)

| Wheat | Sgp-1 | | |
|---|---|---|---|
| | -A1 | -B1 | -D1 |
| SGP-1 null | b | b | b |
| Turkey 116 | a | a | b |
| Kanto 79 | a | b | a |
| Chousen 57 | b | a | a |
| Chousen 30 | b | a | a |
| Chinese Spring | a | a | a |
| Norin 61 | a | a | a |

In Sgp-1 alleles, a indicates standard allele in cv Chinese Spring which produces the protein coded by the gene, while b indicates null allele which does not produce the coding protein. The allele -A1 belongs to A genome -B1 to B genome and -D1 to D genome. Four wheats (Turkey 116–Chousen 30) were used to produce SGP-1 null wheat. Two cultivars (Chinese Spring and Norin 61) were controls for analyzing starch properties.

2. Starch and Starch Granule Preparation

Starches from the distal half of $F_2$ seeds for screening were prepared according to Sulaiman and Morrison (J. Cereal Sci. 12:53–61 (1990)), using 80% CsCl.

For characterization of starch, starch granules were prepared according to Echt and Schwartz, supra. Hammer-crushed wheat seeds were homogenized in a protein extraction buffer (55 mM Tris/HCl, pH 6.8, 2.3% SDS, 5% 2-mercaptoethanol and 10% glycerol). This suspension was passed through a 50 μm nylon mesh to remove large seed coats. After centrifugation at 13,500 rpm for 2 min, a yellowish layer on white starch pellet was removed by spatula, and the remaining white starch pellet was suspended in the extraction buffer. This procedure was repeated twice, then the starch was washed twice by distilled water and twice by acetone and air dried.

3. SDS-polyacrylamide Gel Electrophoresis

SDS-polyacrylamide gel electrophoresis of starch granule proteins (SGPs) was performed as described by Yamamori and Endo, supra. An amount of 5 mg of starch prepared from ten (10) mature grains or 5 mg of starch from a distal half of $F_2$ grain was gelatinized in 70 μl of the protein extraction buffer by heating for 5 min. After centrifugation for 5 min at 13,500 rpm, the supernatant (15μl) was subjected to electrophoresis. For the resolution gel, acrylamide in a concentration of 12.5% and BIS-acrylamide in a low concentration (acrylamide/BIS-acrylamide concentration of 30:0.135) were used. Proteins were visualized by silver staining (Silver stain kit; Wako Pure Chemical Industries, Ltd. Japan).

For characterization of starch, cultivar Chinese Spring or Norin 61 having all of SGP-A1, -B1 and -D1 were used as controls.

4. Results

SDS-PAGE analysis of 968 new $F_2$ seeds from the cross (Kanto 79/Turkey 116)$F_2$//Chousen 30 or Chousen 57 found that four seeds yielded no SGP-1. New $F_2$ seeds were classified into eight categories based on Sgp-1 alleles or the presence or absence of SGP-A1, -B1 and -D1. Since the three genes, Sgp-A1, -B1 and -D1 are located on different chromosomes, the expected ratio for the eight categories is 27:9:9:9:3:3:3:1 (see Table 2). However, the observed number did not fit the expected ratio ($\chi^2$=14.26, P<0.05). Seed fertility of $F_3$ plants derived from new $F_2$ plants (SGP-1 null) was 94%, while fertility of cultivar Chinese Spring was 97%. This shows fertility of the SGP-1 null wheat was normal. The SGP-1 null wheat used in Examples 2–4 below was obtained from (Kanto 79/Turkey 116)$F_2$//Chousen 57.

TABLE 2

Segregation of $F_2$ from (Kanto 79/Turkey 116)$F_2$//Chousen 30 or Chousen 57

| Alleles of Sgp-1 | | | Number of $F_2$ | Expected | $\chi^2$ |
|---|---|---|---|---|---|
| -A1 | -B1 | -D1 | seeds observed | ratio | value |
| a | a | a | 424 | 27 | 0.60 |
| b | a | a | 150 | 9 | 1.41 |
| a | b | a | 125 | 9 | 0.91 |
| a | a | b | 143 | 9 | 0.35 |
| a | b | b | 47 | 3 | 0.06 |
| b | a | b | 38 | 3 | 1.20 |
| b | b | a | 37 | 3 | 1.55 |
| b | b | b | 4 | 1 | 8.18 |
| Total | | | 968 | 64 | 14.26* |

Sgp-A1a, -B1a and -D1a are standard alleles in cv Chinese Spring. Sgp-A1b, -B1b and -D1b are null alleles lacking each SGP-1.
*significant difference from the expected ratio at the 5% level by $\chi^2$ test.

Example 2

Decrease in Other Starch Granule-bound Proteins in SGP-1 Null Wheat

In addition to SGP-1, wheat starch granules carry three granule-bound proteins, i.e., waxy protein, SGP-2 and SGP-3. In new $F_2$, $F_3$ and $F_4$ seeds of the SGP-1 null wheat, SGP-2 and -3 decreased considerably while the waxy protein did not, as observed on a gel of SDS-PAGE. The result for the $F_4$ seeds is seen in lane 5 of FIG. 1. To examine how much the SGP-2 and -3 decreased in the SGP-1 null wheat, 1, ½, ¼, ⅛, 1/16 and 1/32 sample volumes of the cultivar Chinese Spring were subjected to electrophoresis and the thickness of SGP-2 and -3 bands detected by silver staining were compared to one volume from the SGP-1 null wheat. As a result, it was found that the elimination of SGP-1 was accompanied with a decrease of both SGP-2 and -3 to about 1/16 as compared with the cultivar Chinese Spring.

Example 3

Measurement of Blue Value and $\lambda_{max}$ of Wheat Lacking SGP-1 (SGP-1 Null Wheat)

To characterize starch components, the present inventor measured the blue value (absorbance at 680 nm) and maximum absorbance ($\lambda_{max}$) of iodine-starch complex from the SGP-1 null wheat ($F_4$ seeds), its parents and cultivar Chinese Spring (see Table 3). Higher blue value indicates that the apparent amylose content of the SGP-1 null wheat was higher than those of the others.

The absorbance at 680 nm (blue value) and maximum absorbance ($\lambda_{max}$) of the iodine-starch complex were determined according to Konishi et al. (Agric. Biol. Chem. 49:1965–1971, 1985). An amount of 10 mg of starch was gelatinized in 1 ml of 1N NaOH for one hour at 40° C., and neutralized by 9 ml of ⅑ M acetic acid. Then, 1 mg of gelatinized and neutralized starch was mixed with 2 mg of $I_2$ and 20 mg KI, and distilled water was added to make a 25 ml solution. Absorption curves of starch-iodine complexes were measured at 500–700 nm, and blue value and $\lambda_{max}$ were recorded.

Example 4

Measurement of Amylose Content of SGP-1 Null Wheat

To confirm that wheat lacking SGP-1 has a high apparent amylose content, the amylose content was measured by colorimetric method and amperometric titration as follows.

(1) Colorimetric measurement based on iodine coloration was performed following the method of Kuroda et al. (Jpn. J. Breed. 39 (Suppl. 2):142–143, 1989) using an auto-analyzer (Bran Lubbe. Co.). An amount of 35 mg of starch was gelatinized in 5 ml of 0.75 N NaOH and 25% aqueous ethanol, and neutralized by acetic acid. Absorbance at 600 nm of starch iodine complex was measured by colorimeter. For control, two wheat starches were used. A first control, wheat starch purchased from Wako Pure Chemicals Ltd. (Japan) contained 31.2% amylose as determined by the auto-analyzer using potato amylose and amylopectin as standards, and a second control, waxy wheat starch contained 0.6% amylose.

The amylose content of the starch from the SGP-1 null wheat was as high as 37.3% (see Table 3). In contrast, Norin 61 and Chinese Spring had an amylose content of 28.2% and 29.6%, respectively. Thus, the amylose content of the SGP-1 null wheat starch was higher than those of cultivars Norin 61 and Chinese Spring by about 8% to 9%. The three wheat cultivars used as crossing parents, i.e., Turkey 116, Kanto 79 and Chousen 57, had amylose contents ranging from 23.9% to 30.3%.

(2) Amperometric titration (Fukuba and Kainuma, "Quantification of amylose and amylopectin" in Starch Science Handbook (Nakamura M. and Suzuki S., eds) Tokyo: Asakura Shoten, pp174–179, 1977) was performed using defatted starch with an iodine amperometric titration device (Model 3–05, Mitamura Riken Kogyo, Japan). Amylose content of the starch was calculated by assuming that 20 mg of iodine can bind to 100 mg of pure wheat amylose. The starch concentration of the solution used was determined by the phenol-sulfuric acid method (Dubois et al., Anal. Chem. 28:350–356, 1956) with glucose as a standard.

The amylose content of the starch from the SGP-1 null wheat was 37.3% (see Table 3). In contrast, Norin 61 and Chinese Spring had an amylose content of 26.6% and 29.3%, respectively. Thus, the amylose content of the SGP-1 null starch was higher than that of cultivars with SGP-1, Norin 61 and Chinese Spring by about 8% to 11%. The three wheat cultivars used as crossing parents had amylose contents ranging from 23.5% to 29.8%.

TABLE 3

Maximum absorbance ($\lambda$max), absorbance at 680 nm (blue value) of starch-iodine complex and amylose content of wheats ($F_4$ seeds)

| Wheat | $\lambda$max (nm) | Blue value | Amylose content (%) | |
|---|---|---|---|---|
| | | | Colorimetric | Titration |
| SGP-1 null ($F_4$) | 602 ± 6 | 0.485 ± 0.023 | 37.3 ± 0.8 | 37.3 ± 0.8 |
| Turkey 116 | 589 ± 5 | 0.370 ± 0.011 | 30.3 ± 0.2 | 29.8 ± 0.5 |

TABLE 3-continued

Maximum absorbance ($\lambda$max), absorbance at 680 nm (blue value) of starch-iodine complex and amylose content of wheats ($F_4$ seeds)

| Wheat | $\lambda$max (nm) | Blue value | Amylose content (%) | |
|---|---|---|---|---|
| | | | Colorimetric | Titration |
| Kanto 79 | 565 ± 0 | 0.307 ± 0.004 | 23.9 ± 0.5 | 23.5 ± 0.1 |
| Chousen 57 | 591 ± 1 | 0.365 ± 0.003 | 29.4 ± 0.1 | 28.1 ± 0.2 |
| Chinese Spring | 586 ± 3 | 0.358 ± 0.013 | 29.6 ± 0.1 | 29.3 ± 0.3 |
| Norin 61 | —[1] | — | 28.2 ± 0.1 | 26.6 ± 0.2 |

[1]These were not examined.
Values are means ± SD from three replicates for two controls and three parental wheats. For SGP-1 null, values from eight (titration), ten (colorimetric) and 15 ($\lambda$max and blue value) replicates were indicated.

The above-mentioned measurement results all indicate that the apparent amylose content of the SGP-1 null wheat starch is considerably higher than that of normal wheat starch.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. Wheat flour obtained from endosperm of a seed of wheat which is modified to lack SGP-1, comprising wheat starch which has an apparent amylose content of about 35% or more.

2. The wheat flour of claim 1 wherein the apparent amylose content is from about 37% to about 40%.

3. The wheat flour of claim 1, wherein the wheat is a hexaploid wheat which lacks SGP-A1, SGP-B1 and SGP-D1.

4. The wheat flour of claim 3, wherein the hexaploid wheat is obtained by crossing a first wheat lacking a first protein selected from the group consisting of SGP-A1, SGP-B1 and SGP-D1, with a second wheat lacking a second protein which differs from the first protein and is selected from the group consisting of SGP-A1, SGP-B1 and SGP-D1, followed by further crossing the cross of the first wheat and the second wheat with a third wheat lacking a third protein which differs from the first and second proteins and is selected from the group consisting of SGP-A1, SGP-B1 and SGP-D1.

5. The wheat flour of claim 3, wherein the hexaploid wheat is obtained by crossing (i) Chousen 30 or Chousen 57, (ii) Turkey 116, and (iii) Kanto 79 in an arbitrary order.

* * * * *